United States Patent
Sleeper et al.

(10) Patent No.: US 7,845,352 B2
(45) Date of Patent: Dec. 7, 2010

(54) FLEXIBLE CPAP MASK

(75) Inventors: Geoffrey P. Sleeper, Bay Villiage, OH (US); David J. Palkon, Tinley Park, IL (US)

(73) Assignee: CareFusion 205, Inc., San Diego, CA (US)

( * ) Notice: Subject to any disclaimer, the term of this patent is extended or adjusted under 35 U.S.C. 154(b) by 1110 days.

(21) Appl. No.: 11/184,370

(22) Filed: Jul. 19, 2005

(65) Prior Publication Data

US 2006/0027237 A1 Feb. 9, 2006

Related U.S. Application Data

(60) Provisional application No. 60/589,319, filed on Jul. 20, 2004.

(51) Int. Cl.
  *A62B 7/10* (2006.01)
  *A62B 18/08* (2006.01)
  *A62B 18/02* (2006.01)
  *A62B 9/06* (2006.01)
  *A62B 7/00* (2006.01)
  *A61G 10/00* (2006.01)

(52) U.S. Cl. .......................... 128/206.23; 128/205.25; 128/206.11; 128/206.12; 128/206.13; 128/206.18; 128/206.21; 128/206.24; 128/206.27; 128/206.28; 128/207.13; 128/207.16; 128/207.17; 128/207.18

(58) Field of Classification Search ............ 128/206.23, 128/205.25, 206.11–206.13, 206.18, 206.21, 128/206.24, 206.27, 207.13, 207.16–207.18, 128/206.28

See application file for complete search history.

(56) References Cited

U.S. PATENT DOCUMENTS

| 781,516 | A | * | 1/1905 | Guthrie, Jr. | ............ 128/206.18 |
| 5,533,506 | A | | 7/1996 | Wood | |
| 6,431,172 | B1 | | 8/2002 | Bordewick | |
| 6,886,564 | B2 | * | 5/2005 | Sullivan et al. | ........ 128/206.24 |
| 2004/0226566 | A1 | * | 11/2004 | Gunaratnam et al. | ... 128/207.18 |
| 2005/0056286 | A1 | * | 3/2005 | Huddart et al. | ........ 128/206.21 |

OTHER PUBLICATIONS

International Search Report; International Application No. PCT/US05/2555 filed Jul. 20, 2005.

* cited by examiner

*Primary Examiner*—Patricia M Bianco
*Assistant Examiner*—Nihir Patel

(57) ABSTRACT

A respiratory interface device includes a respiratory mask that interfaces with a face of a patient. The respiratory mask comprises a body portion that forms an enclosure around a nose of a patient and at least one set of headgear strap flanges. The body portion is substantially entirely manufactured from an elastomeric material. A bellows-like structure is integrally molded in the body portion to create a sealing interface between an inner bottom portion of the mask and the patient's nose.

13 Claims, 4 Drawing Sheets

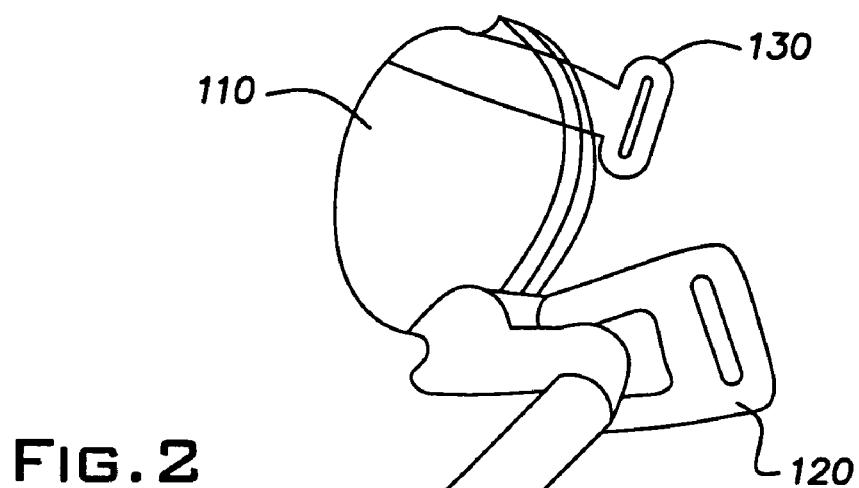
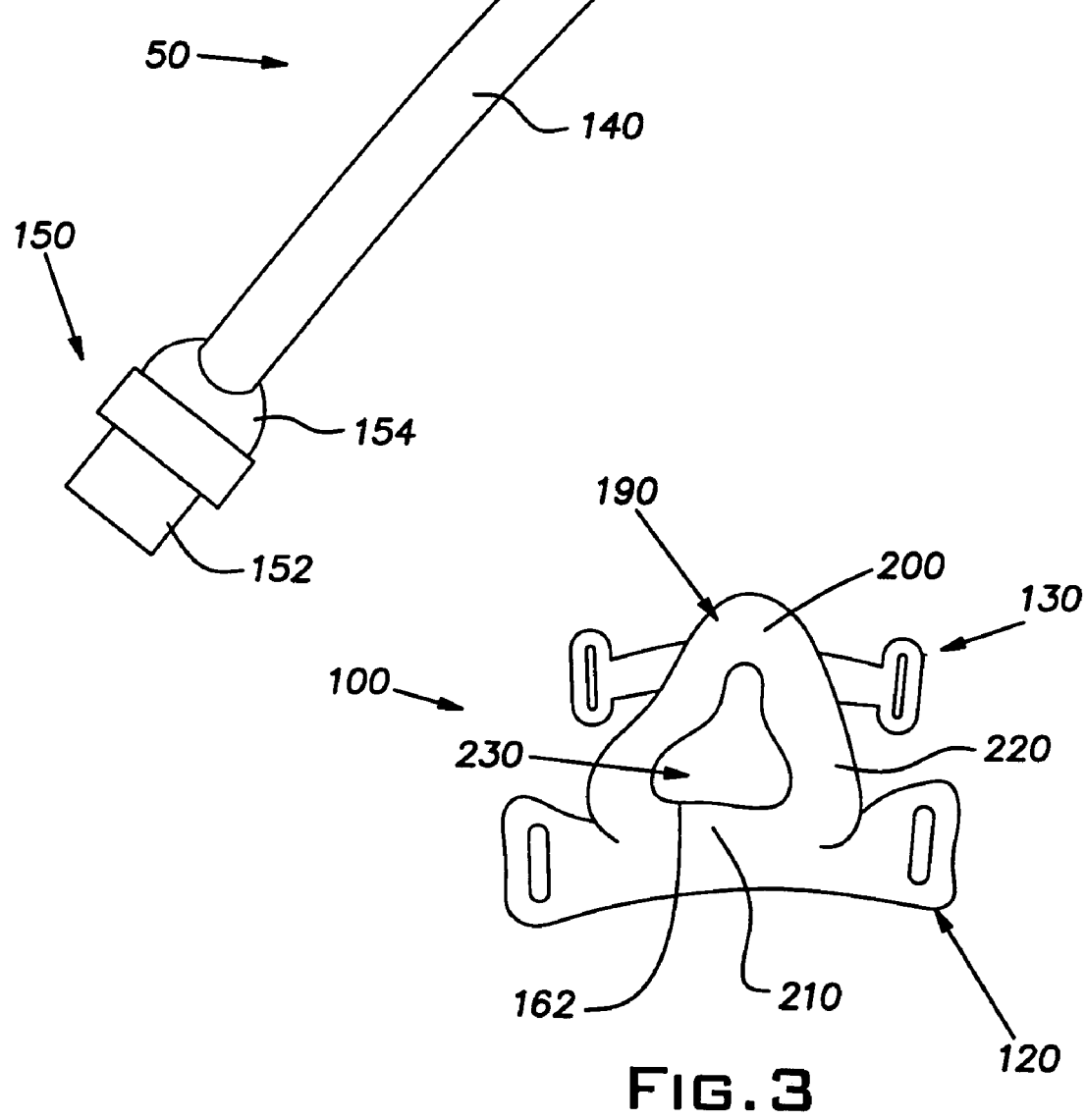

FLEXIBLE CPAP MASK

CROSS REFERENCE TO RELATED APPLICATIONS

The present invention claims priority to U.S. patent application Ser. No. 60/589,319, filed on Jul. 20, 2004.

FIELD OF THE INVENTION

The present invention relates generally to ventilation devices, and more particularly, to a flexible mask for use in a continuous positive airway pressure system.

BACKGROUND OF THE INVENTION

Sleep apnea is a potentially life-threatening breathing disorder characterized by brief interruptions of breathing during sleep. There are two types of sleep apnea: central and obstructive. Central sleep apnea, which is less common, occurs when the brain fails to send the appropriate signals to the breathing muscles to initiate respirations. Obstructive sleep apnea occurs when air cannot flow into or out of the person's nose or mouth although efforts to breathe continue. In a given night, the number of involuntary breathing pauses or "apneic events" may be as high as 20 to 60 or more per hour. Sleep apnea can also be characterized by choking sensations. The frequent interruptions of deep, restorative sleep often leads to excessive daytime sleepiness and may be associated with an early morning headache. Early recognition and treatment of sleep apnea is important because it may be associated with irregular heartbeat, high blood pressure, heart attack, and stroke.

Various forms of positive airway pressure during sleep can be an effective form of therapy for the apnea sufferer. Ventilation can be applied in the form of continuous positive airway pressure (CPAP), in which positive pressure is maintained in the airway throughout the respiratory cycle; bi-level positive airway pressure system, in which positive pressure is maintained during inspiration but reduced during expiration; and intermittent (non-continuous) positive pressure (IPPB), in which pressure is applied when an episode of apnea is sensed. In such procedures, a patient wears a mask over the nose during sleep, and pressure from an air blower forces air through the nasal passages. Typically, such masks receive a gas supply line that delivers gas into a chamber formed by wall of the mask and the patient's face. The walls are usually semi-rigid and have a face-contacting portion include an aperture that is aligned with the patient's nostrils. The face-contacting portion can include a soft, resilient elastomeric material that can conform to various facial contours. The mask is normally secured to the patient's head by straps. The straps are adjusted to pull the mask against the face with sufficient force to achieve a gas tight seal between the mask and the patient's face but not so tight as to be uncomfortable. Gas is thus delivered to the mask and into the patient's nasal passages.

Problems often arise with masks of the above configuration. For example, the face-contacting portion may apply excessive pressure to the wearer's face resulting in discomfort and possibly skin irritation. This can occur because the face-contacting portion has to distort beyond its normal range of elasticity to conform to certain facial contours, which requires the application of excessive forces. In some cases these excessive pressures and forces may cause the face to distort to conform to the face-contacting portion, which can increase wearer discomfort, resulting in facial soreness and ulceration.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a ventilation interface for a continuous positive airway pressure system. According to a first aspect of the present invention, an interface device includes a respiratory mask, which comprises a body adapted to form an enclosure around a nose of a patient, wherein the entire body is manufactured from an elastomeric material; and a bellows-like structure integrally molded in a mustache region of the body.

According to another aspect of the present invention, a respiratory mask is provided. The respiratory mask includes an elastomeric body; a bellows-like structure integrally molded in a mustache region of the body; and at least one headgear strap flange integrally molded with the body.

According to yet another aspect of the present invention, a respiratory mask is provided. The respiratory mask comprises elastomeric mask means for forming an enclosure around a nose of a patient; and bellows integrally molded in the mask means for creating a sealing interface between an inner bottom portion of the mask means and a bottom portion of a patient's nose.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

FIG. 2 illustrates a side view of the flexible CPAP mask of FIG. 1 in accordance with an aspect of the present invention.

FIG. 3 illustrates a back view of the flexible CPAP mask of FIG. 1 in accordance with an aspect of the present invention.

DETAILED DESCRIPTION OF THE INVENTION

Figure 1:
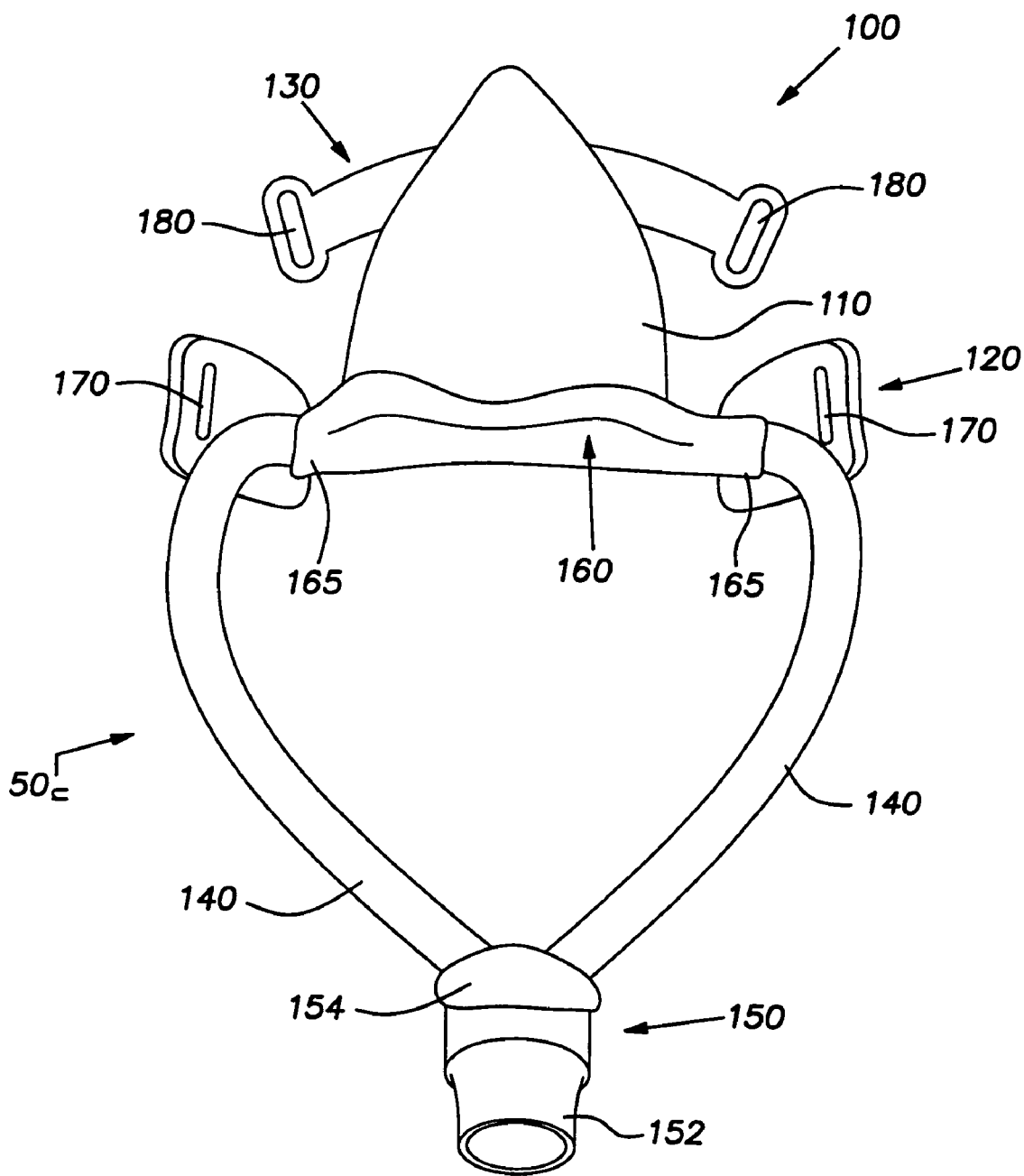
FIG. 1 illustrates a front view of a flexible CPAP mask in accordance with an aspect of the present invention.
Figure 4:
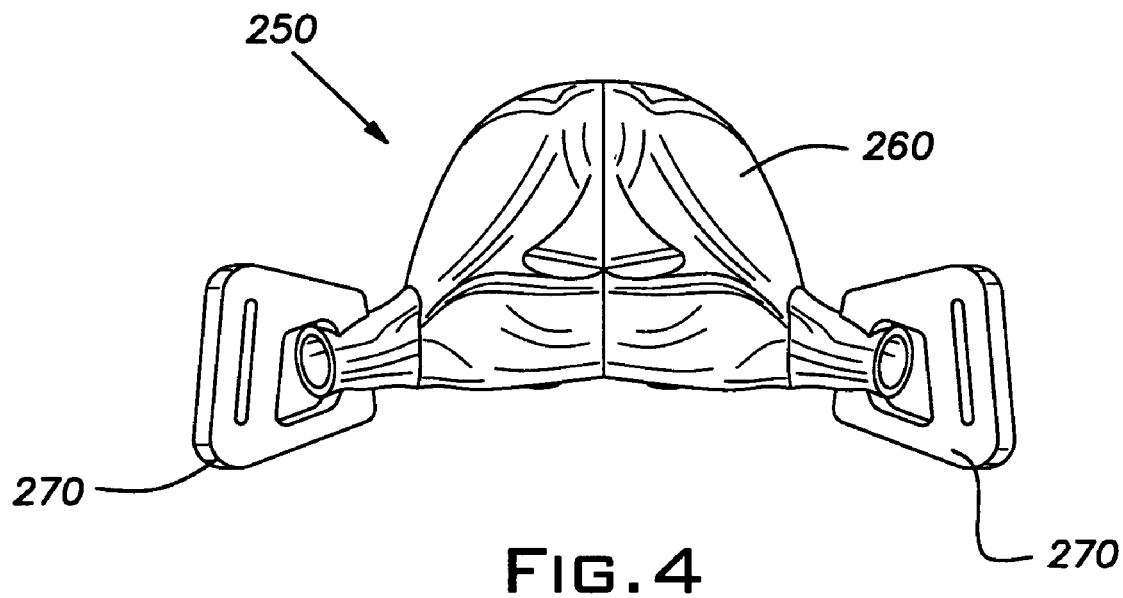
FIG. 4 illustrates a back view of another flexible CPAP mask in accordance with an aspect of the present invention.
Figure 5:
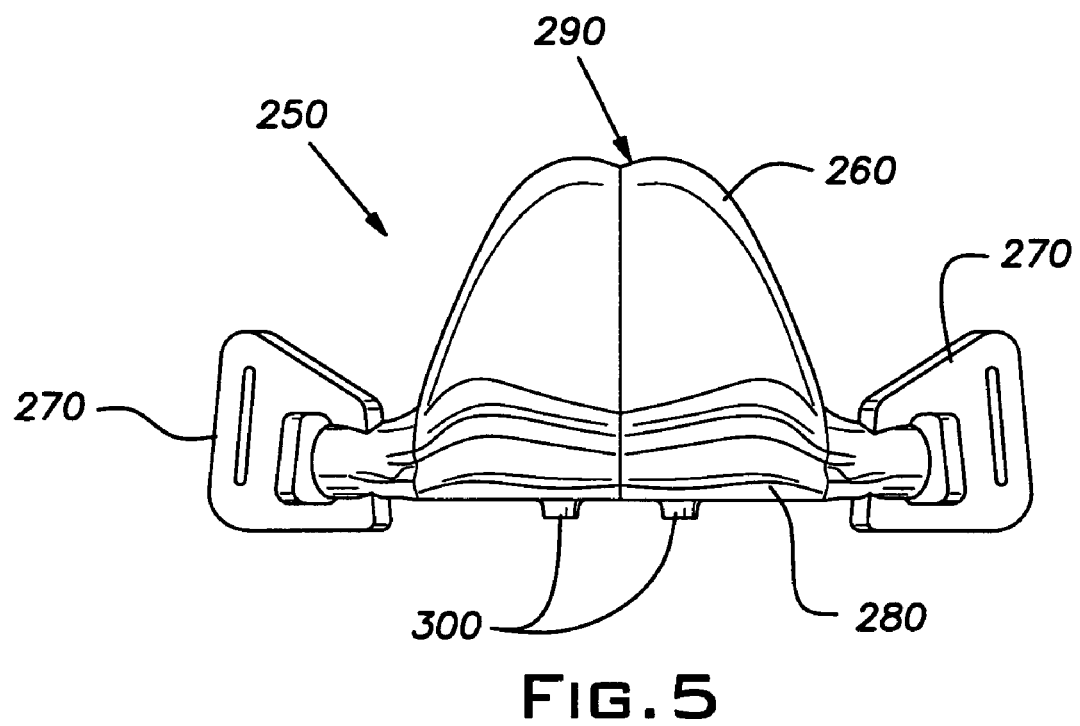
FIG. 5 illustrates a front view of the flexible CPAP mask of FIG. 4 in accordance with an aspect of the present invention.
Figure 6:
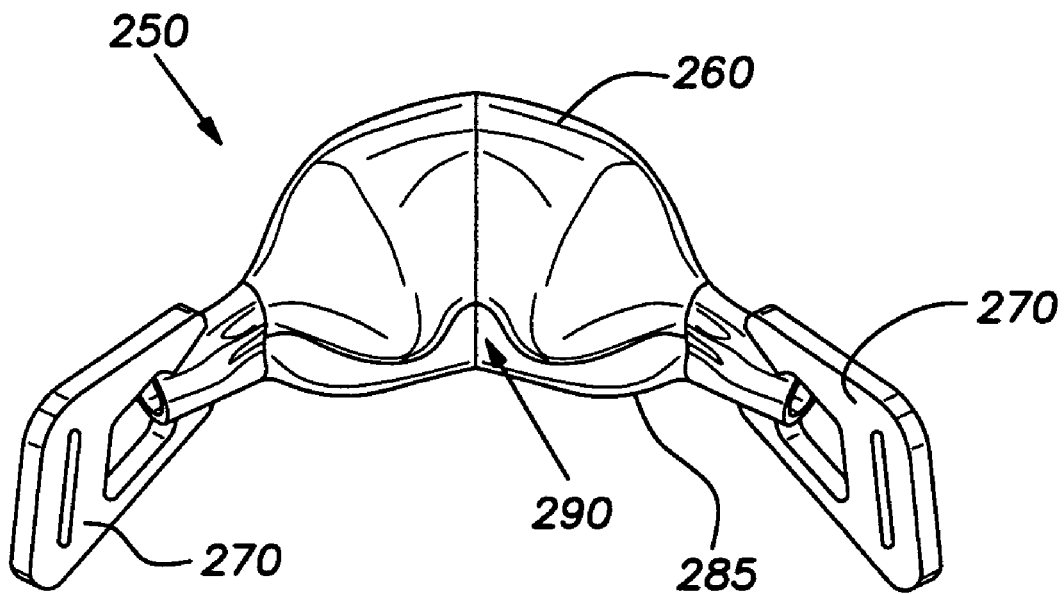
FIG. 6 illustrates a top view of the flexible CPAP mask of FIG. 4 in accordance with an aspect of the present invention.

The present invention provides a flexible mask for use in a continuous positive airway pressure system. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the reading of the drawings. In the following description, for purposes of explanation, numerous specific details are set forth in order to provide a thorough understanding of the present invention. It may be evident, however, that the present invention may be practiced without these specific details.

FIGS. 1-3 illustrate an example of a respiratory interface device 50 in accordance with an aspect of the present invention. The interface device 50 includes a respiratory mask 100 that interfaces with a face of a patient. The respiratory mask 100 comprises a body portion 110 that forms an enclosure around a nose of a patient and at least one set of headgear strap flanges 120, 130. The body portion 110 is manufactured from an elastomeric material such as polyurethane, silicone, or any other suitable material, and can be substantially triangular in shape so as to fit the contours of a patient's face from above the nose to a mustache area, located between the nose and the lips. However, it is to be appreciated that the body portion 110 can be of any other suitable shape (e.g., circular). In contrast to conventional respiratory masks, the body portion 110 of the present invention is not coupled to or does not include a polycarbonate frame, or any other type of rigid shell. Instead, the entire body portion 110 is molded from an elastomeric material, such as silicon; thereby, providing a substantial increase in comfort to the patient.

Two sets of headgear strap flanges 120, 130 can be materially integrally molded with the body portion 110, as depicted in FIGS. 1-3; however, it is to be appreciated that the mask 100 can include any number of headgear strap flanges, including one, if desired. Further, the headgear straps can be coupled to the body portion 110 in any suitable manner. The headgear strap flanges will be described in further detail below.

The interface device 50 also includes one or more supply tubes 140 coupled to the body portion 110 of the mask 100 to deliver air pressure from a ventilation device (not shown) to a patient. In particular, the ventilation device forces a gas, such as air, through the supply tubes 140 and can be provided by a continuous positive airway pressure machine, a bi-level positive airway pressure machine, an intermittent (non-continuous) positive pressure machine, or any other suitable machine to deliver air to the patient via the mask 100. For sleep apnea therapy, the ventilation device will usually supply room air at a pressure of between five and fifteen centimeters of water. The room air may be supplemented with oxygen if desired by splicing an oxygen supply line into the supply hose or using a triple port connector.

A swivel component 150 can be coupled to the supply tube(s) 140 to facilitate easy manipulation of the tubing 140 for patient comfort. Each of the supply tubes 140 includes an end portion, which is coupled to the swivel component 150 to facilitate easy manipulation of the supply tubes 140 for patient comfort. The swivel component 150 comprises a substantially cylindrical element 152 for coupling with a tube of the ventilation device and a hemispherical element 154 having two tubular engaging portions (not shown). The two tubular engaging portions are utilized for coupling with end portions of the supply tubes 140. The cylindrical element 152 and the hemispherical element 154 are operable to swivel with respect to each other. For instance, the cylindrical element 152 and the hemispherical element 154 can swivel about each other by 360°. It is to be appreciated that any suitable structure contemplated for swiveling the mask 100 with the tube of the ventilation device can be utilized.

Turning back to the body portion 110 of the mask 100, a bellows-like structure (hereinafter referred to as "bellows") 160 is integrally molded near the mustache region of the body portion 110 to create a sealing interface between a bottom portion of the mask 100 and the patient's nose. More specifically, the sealing interface is created between an inner bottom surface 162 of the mask 100 and a bottom, triangular shaped area of the nose. The bellows 160 act in a manner similar to a compression spring to apply a gentle upward pressure to the nose thereby holding the sealing surfaces (e.g., the inner bottom surface 162 and the bottom area of the nose) in sealing engagement with one another. The bellows 160 is adjustable in length between a contracted state and an expanded state.

First and/or second sets of headgear strap flanges 120, 130 can be materially integral with, or coupled to, the body portion 110, to facilitate utilization of headgear straps (not shown). The first set of headgear strap flanges 120 can be located at a bottom portion of the body 110. The second set of headgear strap flanges 130 is located at a top portion of the body 110. The flanges 120, 130 include apertures 170, 180, respectively, for receiving the headgear straps. When the mask is positioned around the nose of the patient, the headgear straps fasten around the patient's head and apply pressure to the body portion 110, securing the mask 100 against the patient's face. In particular, the first set of headgear strap flanges 120 are upwardly angled such that a headgear strap coupled to the first set of headgear strap flanges 120 applies a backwards and upwards pressure, at approximately a 45-degree angle, to the bellows portion 160 of the mask 100. The spring-like feature of the bellows 160 partially absorbs this upward pressure and applies gentle pressure to the bottom the nose, thereby, forming an airtight seal between the bottom portion of the body 110 and the patient's nose. The second set of headgear strap flanges 130 are downwardly angled to facilitate a headgear strap applying a backwards and downwards pressure to a top portion of the mask 100, securing the body portion 110 against a nasal bridge region of the patient's nose. Alternatively, the mask can include only one set of headgear strap flanges, as illustrated in FIGS. 4-7.

Also extending from the body 110 of the mask are one or more air inlets 165, two air inlets 165 are illustrated with respect to FIGS. 1-3. The air inlets 165 can extend from a side portion of the body 110 in a substantially upward direction and can be materially integral with the body 110. For instance, one air inlet 165 can be located on each side of the bellows portion 160 of the body 110. It is to be appreciated that one or more air inlets can be located anywhere on the body portion of the body 110 and is contemplated as falling within the scope of the invention. The flexible air supply tubing 140 can be coupled to or materially integral with the air inlets 165. The tubing 140 can be made of a relatively flexible adjustable material, such as plastic or the like, and is employed as a conduit for ventilation.

Although not illustrated, it is to be appreciated that the respiratory interface device 50 can include a Y-connector (not shown) having a first end adapted to receive a supply hose from a mechanical ventilator (not shown) and a second end having a pair of ports (not shown) with connectors for attachment to the air supply tubing. It is to be appreciated that the Y-connector described with respect to the present invention can alternatively be a T-connector, or any other three-way tubing connector as is known in the art. The swivel component 150 can also be coupled to the connector to facilitate easy manipulation of the tubing 140 for patient comfort.

As shown in FIG. 1, the tubing 140 extends for a short distance along a plane defined by the base of the mask 100 and then bends downward. As a result, the weight and torque produced by the supply tubes 140 are supported by at least the first set of headgear straps 120, thereby decreasing a chance of the tubing 140 disturbing the sealing means and potentially breaking the seal between the mask 100 and the patient's face. Alternatively, the supply tubes 140 can be looped over the patient's ears.

Turning now to FIG. 3, a back view of the flexible CPAP mask 100 is depicted in accordance with an aspect of the present invention. The mask 100 includes a face-engaging portion 190. The face-engaging portion 190 includes a nasal bridge region 200 positioned in use above the patient's nose at a bridge portion thereof and a mustache region 210 generally positioned in use between the nares of the nose and the lips. A cheek region 220 separates the nasal bridge region 200 and the mustache region 210. The face-engaging portion 190 is flexible to accommodate a plurality of different facial contours.

In use, the patient's nose is received through an aperture 230 into a chamber within the body 110 of the mask 100. The face-engaging portion 190 thus contacts both a surface of the patient's nose and a portion of the patient's face in the mustache region between the base of the nose and the upper lip, and around the sides and over the bridge of the nose. The shape of the face-engaging portion 190 is particularly suited to seal the region of the facial contour that is the crease between the sides of the nose and the face. The nasal bridge region 200 of the mask 100 can include a strengthening portion to mitigate buckling of the nasal bridge region 200 when the headgear straps apply tension on the mask 100.

The mask 100 of the present invention provides an airtight seal while eliminating the need for the rigid frame employed in conventional masks. A first sealing interface is formed between a top portion of the mask 100 and the patient's face. A first headgear strap fastens around the patient's head and applies backwards pressure to the mask, securing the top portion of the mask 100 against the patient's face. The first headgear strap also applies a downward pressure, at approximately a 45-degree angle, to the bridge region of the patient's face, thereby forming an airtight seal between a top portion of the mask 100 and the patient's nose. A second sealing interface is provided when a top surface of the bellows 160 contacts the bottom, generally triangular shaped surface of the patient's nose, which includes the columella, infratip lobule, and alar sidewall portions of the nose. A second headgear strap fastens around the patient's head and applies backward pressure to mask 100 securing it against the patient's mustache region. Also, the second headgear applies upward pressure, at approximately a 45-degree angle, to the bellows 160. The spring-like feature of the bellows 160 partially absorbs this upward pressure and applies gentle pressure to the bottom the nose, thereby, forming an airtight seal between the bottom portion of the mask 100 and the patient's nose.

FIGS. 4-7 illustrate another example of a respiratory mask 250 in accordance with an aspect of the present invention. The respiratory mask 250 can be manufactured from an elastomeric material such as polyurethane, silicone, or any other suitable material, and is substantially triangular in shape so as to fit the contours of a patient's face from above the nose to a mustache area, located between the nose and the lips. In contrast to conventional respiratory masks, the mask 250 of the present invention does not include a polycarbonate frame, or any other type of rigid shell. Instead, an entire body portion 260 of the mask 250 is molded from an elastomeric material, such as silicon; thereby, providing a substantial increase in comfort to the patient. A set of headgear strap flanges 270 can be integrally molded with the body portion 260.

A bellows-like structure (hereinafter referred to as "bellows") 280 is also integrally molded in the body portion 260 to create a sealing interface between an inner bottom portion 285 (FIG. 6) of the mask 250 and the patient's nose. More specifically, the sealing interface is created between the inner bottom portion 285 of the mask 250 and a bottom, triangular shaped area of the nose. The bellows 280 act in a manner similar to a compression spring to apply a gentle upward pressure to the nose thereby holding the sealing surfaces (e.g., the top surface of the bellows 280 and the bottom area of the nose) in sealing engagement with one another. The bellows 280 is adjustable in length between a contracted state and an expanded state.

A nasal bridge portion of the mask 250 includes a notch 290 for receiving a bridge of the patient's nose.

Figure 7:
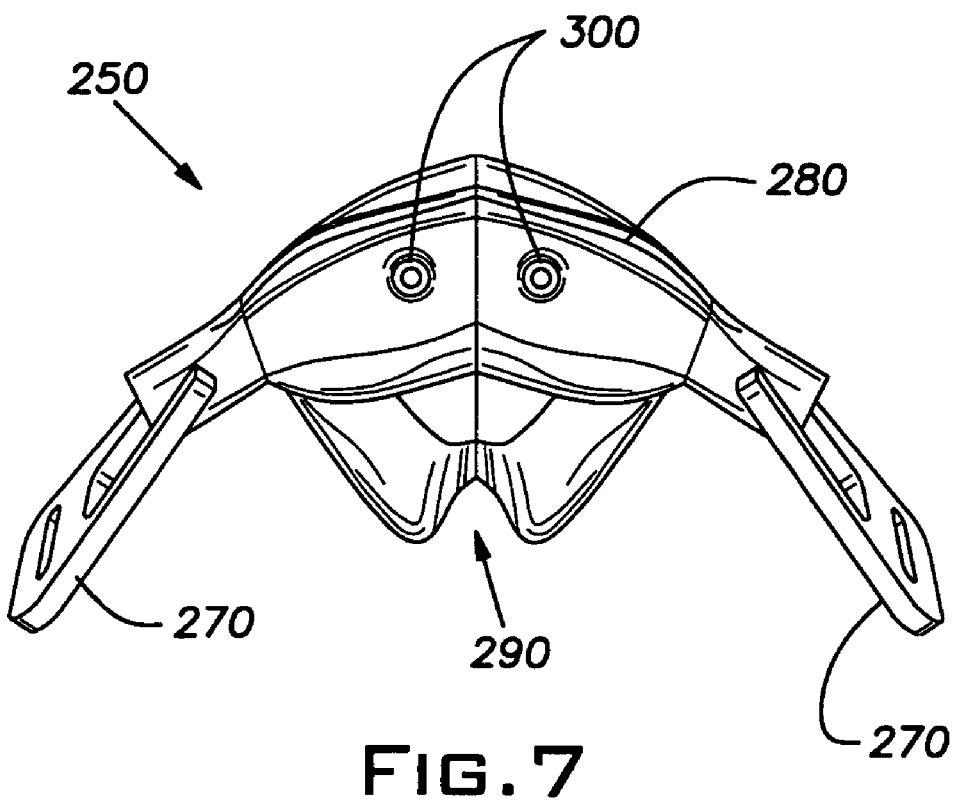
FIG. 7 illustrates a bottom view of the flexible CPAP mask of FIG. 4 in accordance with an aspect of the present invention.

FIG. 7 depicts a bottom perspective view of the mask 250 in accordance with an aspect of the present invention. The mask 250 includes at least one bleeder port 300 projecting from a bottom surface 310 of the body 260. In the example illustrated in FIG. 7, two bleeder ports 300 are utilized and are axially aligned with the patient's nares when positioned within the inner portion of the mask 250. The bleeder ports 300 can be cylindrical and have an internal diameter of about three millimeters and a length of about 0.25 inches, for example. The internal diameter of the bleeder ports 300 are ample to permit venting of carbon dioxide exhaled by the patient while not being so large as to cause a significant pressure drop in the interior of the mask 250. The axial alignment of the bleeder port 300 with the nares creates a direct path for venting of the expired gases. At substantially the same time, laminar flow of air supplied by the supply tubes is normal to the bleeder ports 300, such that air supplied by the ventilator must bend about ninety degrees to exit through the bleeder ports 300. The effect of this construction is that the bleeder ports 300 are virtually silent in operation, mitigating a whistle noise associated with bleeder holes in conventional ventilation interfaces.

Although a detailed description of a preferred embodiment of this invention has been shown and described hereinabove, it will be understood that various modifications and rearrangements of the parts and their respective features may be resorted to without departing from the scope of the invention as disclosed herein.

What is claimed is:

1. An interface device comprising:
a respiratory mask comprising:
a body, including a bottom portion and a top portion, adapted to form an enclosure around a nose of a patient, wherein the entire body is manufactured from an elastomeric material;
a bellows-like structure integrally molded in a mustache region of the body;
one or more supply tubes coupled to the body portion wherein the one or more supply tubes extend for a distance along a plane defined by a base of the mask and then bend downward; and
two sets of headgear strap flanges wherein a first set of headgear strap flanges is located at the bottom portion of the body and a second set of headgear strap flanges is located at the top portion of the body.

2. The interface device of claim 1, wherein the bellows-like structure is adapted to create a sealing interface between a bottom portion of the mask and a patient's nose.

3. The interface device of claim 1, wherein the body is substantially triangular in shape so as to fit contours of a patient's face from above a nose to a mustache area, located between the nose and lips.

4. The interface device of claim 1, wherein the headgear strap flanges are materially integral with the body.

5. The interface device of claim 1, wherein the first set of headgear strap flanges is upwardly angled and the second set of headgear strap flanges is downwardly angled.

6. The interface device of claim 1, further comprising one or more air inlets extending from the body.

7. An interface device comprising:
a respiratory mask comprising:
- a body adapted to form an enclosure around a nose of a patient, wherein the entire body is manufactured from an elastomeric material;
- a bellows-like structure integrally molded in a mustache region of the body; and
- one or more supply tubes coupled to the body portion wherein the one or more supply tubes extend for a distance along a plane defined by a base of the mask and then bend downward,
wherein two air inlets are materially integral with the body such that each air inlet extends from a respective side portion of the body and wherein the two air inlets extend in a substantially upward direction.

8. An interface device comprising:
a respiratory mask comprising:
- a body, including a bottom portion and a top portion, adapted to form an enclosure around a nose of a patient, wherein the entire body is manufactured from an elastomeric material;
- a bellows-like structure integrally molded in a mustache region of the body;
- one or more supply tubes coupled to the body portion;
- a swivel component coupled to the one or more supply tubes; and
- two sets of headgear strap flanges,
wherein a first set of headgear strap flanges is located at the bottom portion of the body and a second set of headgear strap flanges is located at the top portion of the body.

9. The interface device of claim 8, wherein the bellows-like structure is adapted to create a sealing interface between a bottom portion of the mask and a patient's nose.

10. The interface device of claim 8, wherein the body is substantially triangular in shape so as to fit contours of a patient's face from above a nose to a mustache area, located between the nose and lips.

11. The interface device of claim 8, wherein the headgear strap flanges are materially integral with the body.

12. The interface device of claim 8, wherein the first set of headgear strap flanges is upwardly angled and the second set of headgear strap flanges is downwardly angled.

13. An interface device comprising:
a respiratory mask comprising:
- a body adapted to form an enclosure around a nose of a patient, wherein the entire body is manufactured from an elastomeric material;
- a bellows-like structure integrally molded in a mustache region of the body;
- one or more supply tubes coupled to the body portion;
- a swivel component coupled to the one or more supply tubes; and
- two air inlets extending from the body,
wherein the two air inlets are materially integral with the body such that each air inlet extends from a respective side portion of the body, and
wherein the two air inlets extend in a substantially upward direction.

* * * * *